(12) United States Patent
Fischer et al.

(10) Patent No.: US 12,004,506 B2
(45) Date of Patent: Jun. 11, 2024

(54) PHARMACEUTICAL COMPOSITION COMPRISING A CYCLIC PEPTIDE OF FORMULA X1-GQRETPEGAEAKPWY-X2 AND USE FOR EXTRACORPOREAL LUNG TREATMENT

(71) Applicant: APEPTICO FORSCHUNG UND ENTWICKLUNG GMBH, Vienna (AT)

(72) Inventors: Hendrik Fischer, Vienna (AT); Helmut Pietschmann, Vienna (AT); Susan Jane Tzotzos, Vienna (AT); Bernhard Fischer, Vienna (AT); Rudolf Lucas, Martinez (GA)

(73) Assignee: APEPTICO FORSCHUNG UND ENTWICKLUNG GMBH, Vienna (AT)

( * ) Notice: Subject to any disclaimer, the term of this patent is extended or adjusted under 35 U.S.C. 154(b) by 0 days.

(21) Appl. No.: 16/941,074

(22) Filed: Jul. 28, 2020

(65) Prior Publication Data

US 2020/0352156 A1    Nov. 12, 2020

Related U.S. Application Data

(63) Continuation-in-part of application No. 14/784,903, filed as application No. PCT/EP2014/058012 on Apr. 18, 2014, now abandoned.

(30) Foreign Application Priority Data

Apr. 23, 2013    (EP) .................................... 13164828

(51) Int. Cl.
   *A01N 1/02*        (2006.01)
   *C07K 7/64*        (2006.01)
(52) U.S. Cl.
   CPC .............. *A01N 1/0226* (2013.01); *C07K 7/64* (2013.01)
(58) Field of Classification Search
   None
   See application file for complete search history.

(56) References Cited

U.S. PATENT DOCUMENTS

2003/0185791 A1    10/2003   Lucas et al.
2016/0143266 A1    5/2016    Fischer

FOREIGN PATENT DOCUMENTS

WO    WO2006013183    2/2006
WO    WO2010099556    9/2010
WO    WO2011085423    7/2011

OTHER PUBLICATIONS

Egan et al: "Ex vivo evaluation of human lungs for transplant suitability", Ann Thorac Surg. Apr. 2006;81(4):1205-13.
Elia Nadia et al: "Functional identification of the alveolar edema reabsorption activity of murine tumor necrosis factor-alpha", American Journal of Respiratory and Critical Care Medicine, American Lung Association, New York, NY, US, vol. 168, No. 9, Nov. 1, 2003, pp. 1043-1050, XP002455314.
Erasmus et al: "Normothermic ex vivo lung perfusion of non-heart-beating donor lungs in pigs: from pretransplant function analysis towards a 6-h machine preservation", Transpl Int. Jul. 2006;19(7):589-93.
Fiser et al: "Ischemia-reperfusion injury after lung transplantation increases risk of late bronchiolitis obliterans syndrome", Ann Thorac Surg. Apr. 2002;73(4):1041-7; discussion 1047-8.
Hazemi et al: "Essential structural features of TNF-alpha lectin-like domain derived peptides for activation of amiloride-sensitive sodium currecnt in A549 cells", Journal of Medicinal Chemistry, American Chemical Society, vol. 53, No. 22, Oct. 27, 2010, pp. 8021-8029, XP002638326.
Ingemansson et al: "Clinical transplantation of initially rejected donor lungs after reconditioning ex vivo", Ann Thorac Surg. Jan. 2009;87(1):255-60.
Kawut et al: "Outcomes of extended donor lung recipients after lung transplantation", Transplantation. Feb. 15, 2005;79(3):310-6.
King et al: Reperfusion injury significantly impacts clinical outcome after pulmonary transplantation, Ann Thorac Surg. Jun. 2000;69(6):1681-5.
Lederer et al: "Obesity and primary graft dysfunction after lung transplantation: the Lung Transplant Outcomes Group Obesity Study", Am J Respir Crit Care Med. Nov. 1, 2011;184(9):1055-61.
Pierre et al: "Marginal donor lungs: a reassessment", J Thorac Cardiovasc Surg. Mar. 2002;123(3):421-7; 4, 5.
Rega et al: "Long-term Preservation With Interim Evaluation of Lungs From a Non-Heart-Beating Donor After a Warm Ischemic Interval of 90 Minutes", Ann Surg. Dec. 2003;238(6):782-92.

(Continued)

*Primary Examiner* — Julie Ha
*Assistant Examiner* — Tara L Martinez
(74) *Attorney, Agent, or Firm* — Workman Nydegger

(57) ABSTRACT

A method of conditioning/improving lung functions extracorporeally by treatment of a non-ischemic donor lung ex vivo with a cyclized compound of the amino acid sequence of formula $$X_1\text{-GQRETPEGAEAKPWY-}X_2 \qquad \qquad I$$

wherein $X_1$ comprises an amino acid (sequence) with 1 to 4 members, comprising natural or unnatural amino acids, and $X_2$ comprises one amino acid, selected from natural amino acids; and a pharmaceutical composition, comprising a peptide of formula I as defined in any one of claims 1 to 7, in in a form, which is appropriate for spraying to obtain an aerosol for inhalation, or which is appropriate for the preparation of a spray to obtain an aerosol upon spraying, which is appropriate for inhalation.

15 Claims, 2 Drawing Sheets

Specification includes a Sequence Listing.

(56) References Cited

OTHER PUBLICATIONS

Steen et al: "First human transplantation of a nonacceptable donor lung after reconditioning ex vivo", Ann Thorac Surg. Jun. 2007;83(6):2191-48.
Vadasz I et al: "The lectin-like domain of tumor necrosis factor-[alpha] improves alveolar fluid balance in injured isolated rabbit lungs", Critical Care Medicine May 2008 US, vol. 36, No. 5, May 2008, pp. 1543-1550, XP009172075.
Ware et al: "Assessment of lungs rejected for transplantation and implications for donor selection", Lancet. Aug. 24, 2002;360(9333):619-20.
Office Action cited in U.S. Appl. No. 14/784,903 dated Nov. 9, 2016.
Bastin, et al., "Salt selection and optimization procedures of pharmaceutical new chemical entities" Organic Process Research & Development 2000, 4, 427-435.
Final Office Action cited in U.S. Appl. No. 14/784,903 dated Jun. 16, 2017.
Lindstedt et al., "How to recondition ex vivo initially rejected donor lungs for clinical transplantation: Clinical experience from Lung University" Journal of Transplantation; 2011.
Zhang et al., ("How orthoptopic left lung transplantation in rats: a valuable experimental model without using the cuff technique" European Society for Organ Transplantation 21 (2008) 10+0-1997).
Office Action cited in U.S. Appl. No. 14/784,903 dated Mar. 27, 2018.
Final Office Action cited in U.S. Appl. No. 14/784,903 dated Nov. 29, 2018.
Merriam-Webster dictionary (https://www.merriam-webster.com/medical/nonishemic, accessed Nov. 23, 2018) (Year: 2018).
The Merriam-Webster dictionary (https://222.merriam-webster.com/dictionary/ischemia, accessed Nov. 23, 2019). (Year: 2018).
Pan et al., ("Application of ex vivo lung perfusion (EVLP) in lung transplantation" J. Thorac Dis 2018;10(7);4637-4642) (Year: 2018).
Wilkes ( "A Breath of Fresh Air for Lung Transplants Receipients"; Science Translation Medicine, Oct. 28, 2009, vol. 1, Issue 4) (Year: 2009).
Office Action cited in U.S. Appl. No. 14/784,903 dated Jul. 16, 2019.
Final Office Action cited in U.S. Appl. No. 14/784,903 dated Apr. 30, 2020.
Hamacher et al., "The Lectin-like domain of tumor necrosis factor improves lung function after rat lunch transplanation—Potential role for a reduction in reactive oxygen species generation" Crit Care Med, vol. 38, No. 3, (2010) pp. 871-878.

PHARMACEUTICAL COMPOSITION COMPRISING A CYCLIC PEPTIDE OF FORMULA X1-GQRETPEGAEAKPWY-X2 AND USE FOR EXTRACORPOREAL LUNG TREATMENT

CROSS-REFERENCE TO RELATED APPLICATIONS

This Application is a continuation-in-part of U.S. patent application Ser. No. 14/784,903, filed Oct. 15, 2015, which is a 371 Application of International Patent Application No. PCT/EP2014/058012, filed Apr. 18, 2014, which claims the benefit of European Patent Application No. 13164828.9, filed Apr. 23, 2013, which are incorporated by reference in their entirety.

SEQUENCE LISTING

The instant application contains a Sequence Listing that has been submitted electronically in ASCII format and is hereby incorporated by reference in its entirety. Said ASCII copy, created on Oct. 5, 2022, is named "16785-132-1_2022-10-05_Sequence-Listing" and is 4.62 kb in size.

BACKGROUND

The present invention relates to a process for extracorporeal lung treatment for conditioning/improving lung functions before transplantation.

In lung transplantation part or the entire diseased lung is replaced by a healthy lung from a deceased donor to raise quality of life or even survival time of the recipient. The most common indications for lung transplantation are chronic obstructive pulmonary disease (COPD) including emphysema, idiopathic pulmonary fibrosis and cystic fibrosis. Other indications include alpha1-anti-trypsin deficiency emphysema, idiopathic pulmonary arterial hypertension, and sarcoidosis. The mean age of lung donors and recipients is around 35 and 50 years respectively. Unadjusted benchmark survival rates range between about 90% at 3 months and about 30% at 10 years for adult lung transplants. The overall median survival (or "half-life") is currently about 5.5 years. The main causes of deaths after lung transplantation in adult recipients within the first 30 days and in the first year are graft failure and non-cytomegalovirus infections. After 1 year bronchiolitis obliterans (BOS) becomes another major risk factor for morbidity and mortality (Am J Respir Crit Care Med. 2011 Nov. 1;184(9):1055-61).

Restoration of blood supply to an organ after a critical period of ischemia results in parenchymal injury and dysfunction of the organ referred to as reperfusion injury (RI). Ischemia reperfusion injury (IRI) is often seen in organ transplants, major organ resections and in shock. Despite refinements in lung preservation and improvements in surgical techniques and perioperative care, ischemia reperfusion-induced lung injury remains a significant cause of early morbidity and mortality after lung transplantation. The syndrome typically occurs within the first 72 hours after transplantation and is characterized by nonspecific alveolar damage, lung edema, and hypoxemia. The clinical spectrum can range from mild hypoxemia associated with few infiltrates on chest X-ray to a very serious condition requiring positive pressure ventilation, pharmacologic therapy, and occasionally extracorporeal membrane oxygenation (King R C et al, Ann Thorac Surg. 2000 June; 69(6): 1681-5). A number of terms have been used to describe this syndrome, but ischemia reperfusion injury is most commonly used, with primary graft failure attributed to the most severe form of injury that frequently leads to death or prolonged mechanical ventilation beyond 72 hours. In addition to significant morbidity and mortality in the early postoperative period, severe ischemia reperfusion injury can also be associated with an increased risk of acute rejection that may lead to graft dysfunction in the long term (Fiser S M et al, Ann Thorac Surg. 2002 April; 73(4): 1041-7; discussion 1047-8).

IRI is characterized by poor oxygenation as the main criterion for the condition and is also characterized by low pulmonary compliance, interstitial/alveolar edema, pulmonary infiltrates on chest radiographs, increased pulmonary vascular resistance, intrapulmonary shunt and acute alveolar injury, as revealed by diffuse alveolar damage (IDAD) on pathology. Clinically, patients face prolonged ventilation, prolonged stays in the ICU and the hospital overall, increased medical costs, and increased risk of morbidity and mortality.

Lung transplantation has become the mainstay of therapy for patients suffering from endstage lung disease refractory to medical management. However, the number of patients listed for lung transplantation largely exceeds the donors available. Worldwide only 15 to 20% of the lungs that are offered from brain dead donors are used, while 80% of lungs are rejected because they do not meet the donor selection criteria. Damage of the donor lung is manifested by clinical findings such as poor gas exchange or chest x-ray infiltrates which can lead to graft dysfunction and failure post-transplant. A number of strategies have been advocated to increase the number of donor lungs. Some lung transplantations are linked to living related lung donor programs, whereas others are focused on non-heart-beating donors as strategies to ultimately help to palliate the lack of donors. Although living related donors have been used successfully at some centers and use of non-heart-beating donors has been shown to be feasible in humans, overall these strategies have remained limited to a small number of patients due to technical, medical and ethical considerations.

Although the use of extended donor lungs has led to a gradual increase in overall lung transplant activities over the past 10 years, some studies have demonstrated that the liberal use of these lungs can lead to a longer ICU stay, higher early mortality and worse spirometry at 1 year (Kawut S M et al, Transplantation. 2005 Feb. 15:79(3):310-6; Pierre A F et al, J Thorac Cardiovasc Surg. 2002 March, 123(3):421-7; 4, 5).

Therefore, each donor is carefully considered individually and the risk that one may take in choosing an extended donor lung for transplantation should be always weighed against the risk of recipient death while on the waiting list. An accurate assessment of the donor lung is a key element in selecting organs that can be used safely for transplantation. Unfortunately, prediction of post transplant outcomes using the current clinical donor selection criteria is imprecise and some criteria such as chest radiograph evaluation and bronchoscopy findings are quite subjective. The inaccuracy of clinical parameters in determining post-transplant outcomes occasionally leads to the use of lungs with unrecognized injuries leading to severe primary graft dysfunction (PGD). More importantly, it is estimated that about 40% of the lungs that are currently clinically rejected for transplantation could have been safely utilized (Ware L B et al, Lancet. 2002 Aug. 24:360(9333): 619-20) if a more detailed evaluation of the organ would have been possible. These lungs would significantly increase the total donor lung availability.

Based on the general idea to use lungs from donors after cardiac arrest, the "ex vivo" perfusion (EVLP) technique can be used in order to evaluate the lung function of lungs that otherwise could not be evaluated "in vivo". After a short period of 60 to 90 minutes of "ex vivo" evaluation, donated lung may be successfully used in human lung transplantation (Steen S et al, Ann Thorac Surg. 2007 June; 83(6):2191-48; Ingemansson R et al, Ann Thorac Surg. 2009 January; 87(1):255-60).

Other studies have also demonstrated experimentally the feasibility of short-term "ex vivo" perfusion with adequate solutions in order to evaluate lung function in animal models and clinically unsuitable human lungs (Rega F R et al, Ann Surg. 2003 December; 238(6): 782-92; Erasmus M E et al, Transpl Int. 2006 July; 19(7): 589-93; Egan T M et al, Ann Thorac Surg. 2006 April; 81(4):1205-1310-12).

This concept of EVLP technique followed by lung transplantation has been successfully transferred into clinical practice. However, until now EVLP is being used only to evaluate donor lung function "ex vivo" and EVLP has not been used for re-conditioning donor lungs and/or to administer therapeuticall active drugs into the lung.

Peptides as exemplified herein are already disclosed as pharmaceuticals in
WO 2006/013183 (administration of a peptide together with a pulmonary surfactant),
WO 2010/099556 (treatment of hyperpermeability),
WO 2011/085423 there is described (pulmonary or parenteral application),
Parastoo et al, J. Med. Chem. 2010, 53, 8021-8029 (activation of the amiloride-sesitive sodium flow in A549 cells).

Extracorporeal lung treatment, however is not described in any of these publications In Vadasz et al, Crit Car Med 2008, vol 36 no. 5, 1543-1550 and in Elia et al, Am J Resp and Crit Car Med 2003, vol 168, Nr. 9, 1043-1050 animal models are described, wherein a lung extracorporeally is treated in order to show activity of the peptides used. An extracorporeal treatment for improving lung functions and transplantation of the thus treated lung into a recipient is not indicated and not intended. Moreover, the lungs as used according to these publications are inappropriate for re-implantation due to damage of the epithelial/endothelial barrier.

SUMMARY

It was now surprisingly found, that non-ischemic donor lungs may be perfused and ventilated "ex vivo" prior to implantation and that such ex vivo treatment of non-ischemic lungs may be conditioned prior to implantation by administration of bio-active compounds to improve ventilation performance of the lung prior to transplantation and prevent or substantially reduce ischemia reperfusion-induced lung injury.

DETAILED DESCRIPTION

Figure 1:
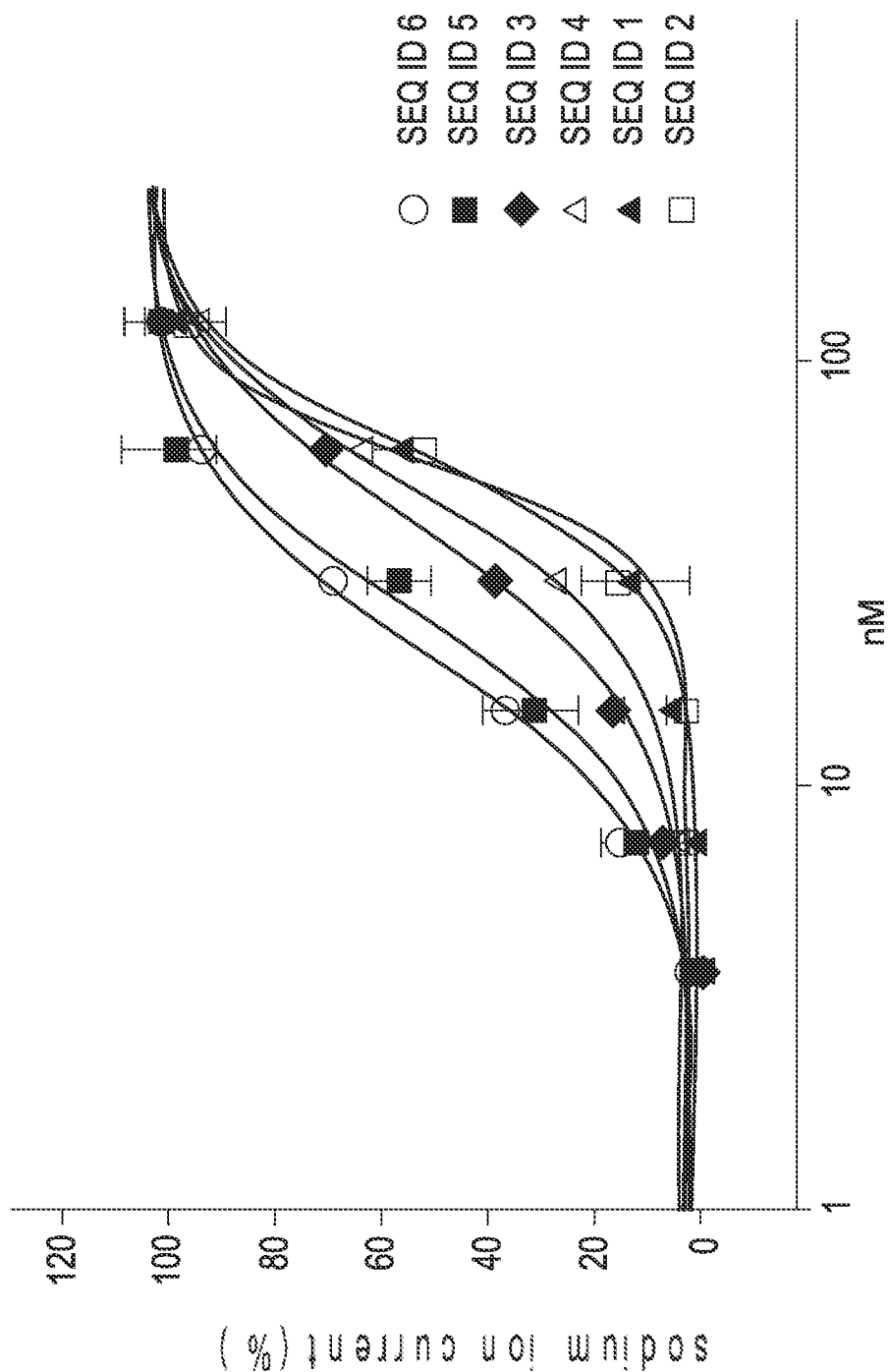
FIG. 1 graphically illustrates the activity of the cyclic peptides of amino acid sequence SEQ ID NO:1 to SEQ ID NO:6 in dependency from the concentration applied.

In one aspect the present invention provides a method of conditioning/improving lung functions extracorporeally comprising treating a non-ischemic donor lung ex vivo with a cyclized compound of the amino acid sequence (SEQ ID NO:9) of formula I:

$$X_1\text{-GQRETPEGAEAKPWY-}X_2 \quad \text{I}$$

wherein
$X_1$ comprises an amino acid sequence with 1 to 4, in particular 1 to 3 members, comprising natural or unnatural amino acids, in particular selected from the amino acid sequence C, KSP, K, omithin, 4-amino butanoic acid, β-alanine, and
$X_2$ comprises one amino acid, selected from natural amino acids, in particular selected from the group C, D, G and E,
and wherein
$X_1$ comprises the N-terminal amino acid at ist first left position and $X_2$ comprises the C-terminal amino acid at its last right position.

Natural amino acids useful in an amino acid sequence in a method of the present invention are known and comprise e.g. G, A, V, L, I, M, P, F, W S, T, N, Q, C, U, Y, D, E, H, K, R.

Unnatural amino acids useful in an amino acid sequence in a method of the present invention comprise
amino acids which have the principal structure of natural amino acids, but which are other than alpha amino acids,
natural amino acids in the D-form, namely other than in the natural L-form, i.e. natural amino acids, wherein the alkyl group is not in the L-configuration, but in the D-configuration,
unnatural amino acids comprising from 2 to 12, such as from 2 to 6 carbon atoms, at least one amino group, e.g. one or two, and at least one carboxy group, e.g. one or two, e.g. optionally beside substituents which are present also in natural amino acids, such as e.g. OH, —CONH$_2$, —NH—C(=NH$_2$)NH$_2$, SH, (C$_{1-4}$)alkyl-S—, phenyl, heterocyclyl, e.g. comprising 5 or 6 ring members and comprising at least on heteroatom selected from N, O, S, preferably N, e.g. one or two N, optionally anellated with another ring, such as phenyl, e.g. including prolinyl, indolyl, imidazolyl.

Unnatural amino acids in an amino acid sequence in a method of the present invention include ortithin, 4-aminobutyric acid, β-alanine.

In another aspect a cyclized compound of the amino acid sequence (SEQ ID NO:9) of formula I includes
a sequence SEQ ID NO: 1
Cyclo(CGQRETPEGAEAKPWYC)
wherein both terminal cysteine residues form a disulphide bridge:
a sequence SEQ ID NO:2
Cyclo(KSPGQRETPEGAEAKPWYE)
wherein an amide bond is formed between the amino group attached to the ε-carbon atom of the N-terminal lysine residue and the side chain carboxyl group attached to the γ-carbon of the C-terminal glutamic acid residue;
a sequence SEQ ID NO:3
Cyclo(KGQRETPEGAEAKPWYG)
wherein an amide bond is formed between the amino group attached to the &-carbon atom of the side chain of the N-terminal lysine residue and the carboxyl group of the C-terminal glycine residue;

a sequence SEQ ID NO:4

Cyclo(ornithine-GQRETPEGAEAKPWYG)

wherein an amide bond is formed between the amino group attached to the δ-carbon of the side chain of the N-terminal ornithine residue and the carboxyl group of the C-terminal glycine residue;

a sequence SEQ ID NO:5

Cyclo(4-aminobutanoic acid-GQRETPEGAEAK-PWYD)

wherein an amide bond is formed between the amino group of the N-terminal 4-aminobutanoic acid residue and the side chain carboxyl group attached to the β-carbon of the C-terminal aspartic acid residue; and a sequence SEQ ID NO:6

Cyclo(β-alanine-GQRETPEGAEAKPWYE)

wherein an amide bond is formed between the amino group of the N-terminal β-alanine (3-aminopropanoic acid) residue and the side chain carboxyl group attached to the γ-carbon of the C-terminal glutamic acid residue.

A sequence SEQ ID NO:7

Cyclo(CGQREAPAGAAAKPWYC)

wherein a disulphide bridge is formed between both terminal cysteine residues was prepared for comparison only and does not form part of the present invention.

A cyclised compound useful in a method according to the present invention is designated herein also as "cyclized compound(s) of (according to) the present invention" and includes a compound in any form, e.g. in free form and in the form a salt, e.g. in biological environment a compound of the present invention normally is in the form of a salt.

In another aspect a cyclised compound of the present invention is in the form of a salt.

Such salts include preferably pharmaceutically acceptable salts, although pharmaceutically unacceptable salts are included, e.g. for preparation/isolation/purification purposes.

In biological environment a salt of a cyclized compound of the present invention is normally a hydrochloride.

A cylised compound of the present invention in free form may be converted into a corresponding cyclised compound in the form of a salt; and vice versa.

A cyclised compound of the present invention may exist in the form of isomers and mixtures thereof; e.g. optical isomers. A cyclised compound of the present invention may e.g. contain asymmetric carbon atoms and may thus exist in the form of enantiomers or diastereoisomers and mixtures thereof, e.g. racemates. A cyclised compound of the present invention may be present in the (R)-, (S)- or (R,S)-configuration preferably in the (R)- or (S)-configuration regarding each of the substituents at such asymmetric carbon atoms in a cyclized compound of the present invention. Isomeric mixtures may be separated as appropriate, e.g. according, e.g. analogously, to a method as conventional, to obtain pure isomers. The present invention includes a compound of the present invention in any isomeric form and in any isomeric mixture. In case of natural amino acids the configuration of substituents is as in natural amino acids.

A cyclised compound of the present invention may be prepared as appropriate, e.g. according, e.g. analogously, to a method as conventional, e.g. or as specified herein, e.g. by solid-phase peptide synthesis, optionally according to the fluorenylmethoxy carbonyl/t-butyl protection strategy on 2-chlorotritylchloride resin using appropriate coupling agents, such as diisopropyl carbodiimide and/or N-hydroxybenzotriazole and appropriate solvent, e.g. N,N-dimethylformamide. Protected amino acids may be coupled in succession to the peptide chain, starting with the C-terminal amino acid. Deprotection from fluorenylmethoxy carbonyl-protected groups may be carried out with a base, e.g. piperidine, such as 20% piperidine in an appropriate solvent, such as N—N-dimethyl formamide. The cleavage of the completed, optionally (partially) protected peptide from the resin may be carried out as appropriate, e.g. with an acid, such as acetic acid in appropriate solvent, e.g. halogenated hydrocarbon, such as $CH_2Cl_2$, e.g. in a 1:1 mixture of acetic acid and $CH_2Cl_2$.

In the case of cysteine-containing peptides, after cleavage from the resin, side-chain deprotection may be carried out, if necessary, e.g. with a strong acid, such as trifluoroacetic acid (TFA), e.g. 95% TFA/5% $H_2O$. Cyclization to obtain a disulfide bond may be carried out by oxidation of terminal cysteine residues, e.g. achievable by aeration of the crude linear peptide at pH 8.5 for 90 hours. Crude peptide product obtained may be purified, e.g. by chromatography, e.g. by reverse phase medium pressure liquid chromatography (RP-MPLC) on an appropriate column, such as RP-C18-silica gel column, conveniently using an eluent gradient, such as a gradient of 5% to 40% aqueous acetonitrile. A trifluoracetate counter-ion may be replaced, e.g. by acetate, e.g. over a column, such as over a Lewatit MP64 column (acetate form). Following a final wash in water, the purified peptide as acetate salt may be lyophilized and may be obtained in the form of a light coloured, e.g. white powder.

In the case of cysteine-free peptides, the cyclization step may be carried out as appropriate, e.g. still on the partially-protected linear peptide, following the cleavage from the resin. After selective cyclization of the cysteine-free peptides, side-chain deprotection in TFA, if necessary, may be carried. A purification step may be carried out, e.g. via chromatography, e.g. by preparative RP-MPLC. From the peptide thus obtained replacement of the trifluoroacetate ion by acetate may be carried out, e.g. as described above. Lyophilization of the acetate form of the peptide may also be carried out, e.g. as for cysteine-containing peptides.

The molecular masses of peptides obtained may be confirmed by electrospray ionisation mass spectrometry or MALDI-TOF-MS. Purity may be determined, e.g. by analytical high performance liquid chromatography.

The cyclised compounds of the present invention, e.g. including a compound of formula I, exhibit interesting pharmacological activity and are therefore useful as pharmaceuticals. E.g., study results as indicated in the examples demonstrated that upon inhalative application of a cyclised compound of the present invention both, dynamic lung compliance and arterio-venous pO2 difference ΔpO2 improved in lungs. Also it was shown that cellular sodium ion current was enhanced when administering a cyclised compound of the present invention. Surprisingly, and despite the rather similar amino acid sequence in a compound with the amino acid sequence SEQ ID NO:7 compared with compounds with the amino acid sequences SEQ ID NO: 1 to SEQ ID NO:6 the compound with the amino acid sequence SEQ ID NO:7 did not show activity in assays wherein the compounds with the amino acid sequences SEQ ID NO: 1 to SEQ ID NO:6 did show good activity.

A cyclised compound of the present invention is thus indicated for conditioning/improving lung functions extracorporeally, e.g. before transplantation.

It was surprisingly found that administration of a cyclised compound of the present invention at best may be performed by inhalative administration, e.g. administration which is adequate to inhalative administration, respectively, namely atomizing (spraying) onto the lung tissue.

It was found surprisingly that an active or passive transport of a cyclised compound of the present invention, for example with (one of) the amino acid sequence SEQ ID NO:1 to SEQ ID NO:6 through the lung tissue into the blood is not desirable and should not happen because it was found that, if the cyclised compound arrives in the lung airspace via oral inhalation, so that it separates onto the surface of the lung tissue and thus is enabled to activate the apikal oriented amilorid-sensitive Sodium Ion Channel, it contributes to a great extent to the physiological effectiveness of a cyclised compound of the present invention, e.g. of the amino acid sequences SEQ ID 1 to SEQ ID 6.

For that, firstly a cyclised compound of the present invention, e.g. of (one of) the amino acid sequences SEQ ID NO:1 to SEQ ID NO:6 is dissolved in water, in order to obtain an aqueous solution and the solution obtained is optionally filtered, e.g. in order to remove impurities. The filtrate obtained is optionally lyophilized, e.g. for the case that a storage form is desired. Surprisingly it has been found that a lyophilized cyclised compound of the present invention thus obtained is stable for a long period. Stability of the lyophilisates was determined after up to 24 months at 2 to 8° C. and up to 6 months at 25° C. at 60% relative humidity. For that usual laboratory analytical methods were used, e.g. visual inspection and reversed HPLC.

After a storage of 24 months at 2 to 8° C. also the die biological activity via Patch Clamp experiments was determined. The lyophilisates turned out to be stable under the conditions described, the appearance did not change, the content of the cyclised peptide of formula I and purity showed only small variances, if even. Also the biological activity remained practically unchanged.

Stability investigations of an aqueous solution of a cyclised compound with the amino acid sequence SEQ ID NO: 1 is set out in Table I below.

TABLE I

| Parameter | Laboratory Syringe Temperature 2 to 8° C. | | Storage tank of a nebulizer Temperaturd 25° C. | |
|---|---|---|---|---|
| | T = 0 | T = 7 days | T = 0 | T = 24 hours |
| Appearanced | Clear solution | | Clear solution | |
| Amount/Content | 25 mg/ml | | 25 mg/ml | |
| Purity | 96.3% | 96.2% | 96.6% | 96.5% |

With the aid of nebulizers the aqueous solution of a cyclised compound of formula I, namely that of the amino acid sequence SEQ ID NO: 1 was transferred into an aerosol. The particle size of the droplets was measured after subjecting the aqueous solution to 3 different nebulizers and is set out in Table II below:

TABLE II

| Nebulizer | Median Particle diameter | Amount of particles with Ø ≤ 5 μm |
|---|---|---|
| Type A | 4.7 μm | 50% |
| Type B | 3.3 μm | 70% |
| Type C | 3.7 μm | 65% |

Evidence could be provided by appropriate experiments that the a cyclised compound of formula I in the lung tissue was present, but practically not in the blood after inhalation as an aerosol. With parenteral administration it was found that a cyclised compound of formula I mainly was present in the blood.

For administration by inhalation/spraying, e.g. in the form of an aerosol, either the aqueous solution from the first dissolution step, or the lyophilisates obtained, re-dissolved in water, is subjected to spraying (atomizing) to obtain an aerosol, e.g. by use of a nebulizer. Surprisingly it was found that the aqueous solution of a cyclised compound of the present invention, e.g. of (one of) the amino acid sequences SEQ ID NO:1 to SEQ ID NO:6 is also stable for a rather long time, even without addition of stabilizers and/or auxiliaries which usually are used. It was also found that the size of the vaporized droplets comprising a dissolved cyclized compound of the present invention also may have an advantageous influence. E.g. in a preferred embodiment the droplet size of (most of) the atomized droplets does not exceed 5 μm (upper limit), in order to obtain a particularly successful result. The appropriate lower limit of the droplet size is dependent only from the feasibility of the droplets.

Figure 2A:
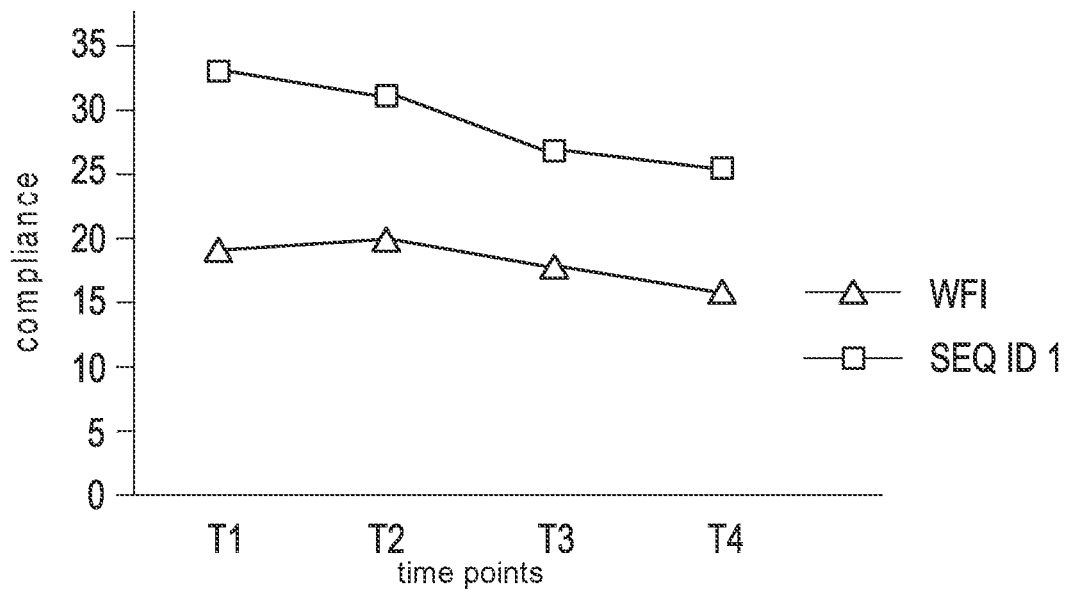
FIGS. 2A and 2B illustrate results form inhalative application of a peptide of SEQ ID NO: 1 during extra-corporal lung perfusion (ex vivo) of a non-ischemic lung, simulating lung transplantation.
Figure 2B:
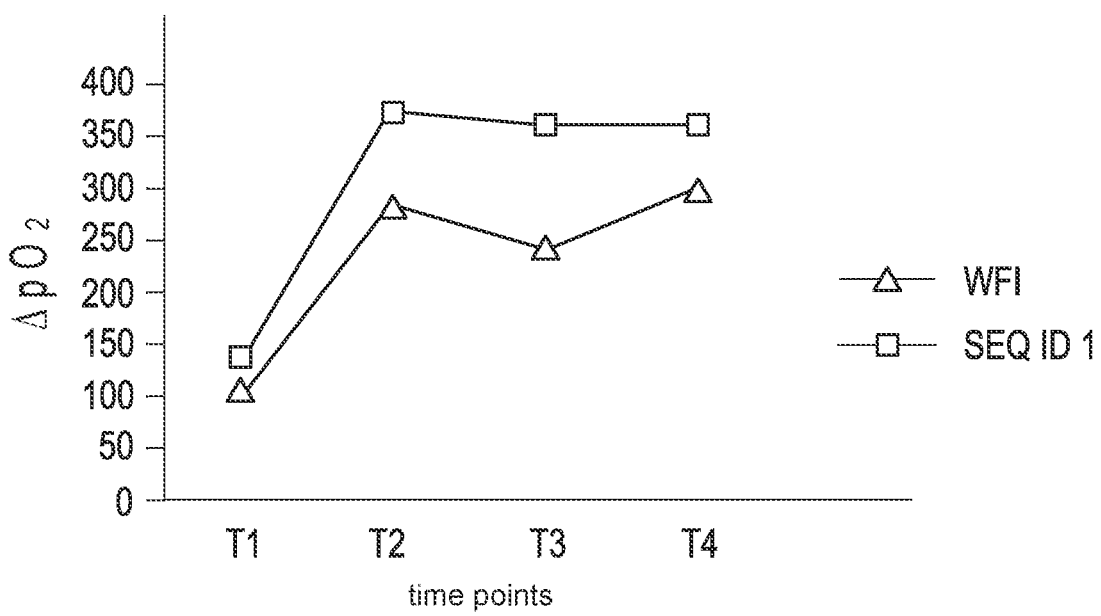

It could be shown in a study by which effects of a cyclised compound of the present invention, in particular with the amino acid sequence SEQ ID NO:1 on the lung function of pig lungs in an extracorporeal system which is simulating lung transplantation, that via administration by inhalation/spraying, i.e. by use of an aerosol, the dynamic lung conformity as well as the artero-venous pO2 difference ΔpO2 were improved, e.g. as shown in FIG. 2A and FIG. 2B.

In another aspect the present invention provides a pharmaceutical composition, comprising a, e.g. at least one, compound of formula I in a form, which is appropriate for spraying (inhaling) to obtain an aerosol, or which is appropriate for the preparation of an aerosol, which aerosol is appropriate for spraying (inhaling), e.g. wherein the size of the droplets does not exceed 5 μm.

It was surprising, that in an aerosol provided by the present invention no stabilizers or other auxiliaries need to be present.

With reference to the drawings, FIG. 1 shows the activity of the cyclic peptides of amino acid sequence SEQ ID NO: 1 to SEQ ID NO:6 in dependency from the concentration applied. On the x-axis the concentration in nM (logarithmic scale) of the cyclic proteins of SEQ ID NO: 1 to SEQ ID NO:6 is indicated, on the y-axis the sodium ion current in %.

FIGS. 2A and 2B show results form inhalative application of a peptide of SEQ ID NO: 1 during extra-corporal lung perfusion (ex vivo) of a non-ischemic lung, simulating lung transplantation.

In FIG. 2A on the x-axis time points T1 to T4 are indicated where measurements—every hour—were made and on the y-axis the compliance.

In FIG. 2B on the x-axis again the time points T1 to T4 and on the y-axis the arterio-venous $pO_2$ difference $\Delta pO_2$. Measurements were carried out once every hour after inhalative administration of the peptide SEQ ID NO:1. Water for Injection (WFI) was used as a control. Means of 8 experiments per group are shown.

In the following examples all temperatures are in ° C. (degree Celsius).

Example 1—Peptide Synthesis

All peptides were synthesised by solid-phase peptide synthesis according to the fluorenylmethoxycarbonyl/t-butyl protection strategy on 2-chlorotritylchloride resin. Diisopropyl carbodiimide and N-hydroxy benzotriazole were used as coupling reagents. All coupling steps were carried out in N—N-dimethyl formamide. Protected amino acids were coupled in succession to the peptide chain, starting with the C-terminal amino acid. Deprotection of fluorenylmethoxycarbonyl was carried out in 20% piperidine in N—N-dimethyl formamide. Cleavage of the completed, partially-protected peptide from the resin was carried out in a 1:1 mixture of acetic acid and dichloromethane. In the case of cysteine-containing peptides, after cleavage from the resin, side-chain deprotection in 95% trifluoroacetic acid, 5% water, was carried out followed by cyclisation by oxidation of terminal cysteine residues, achieved by aeration of the crude linear peptide at pH 8.5 for 90 hours. Crude peptide product was purified by reverse phase medium pressure liquid chromatography (RP-MPLC) on an RP-C18-silica gel column with a gradient of 5%-40% acetonitrile. Finally, the trifluoracetate counter-ion was replaced by acetate on a Lewatit MP64 column (acetate form). Following a final wash in water, the purified peptide as acetate salt was lyophilised and obtained as a white to off-white powder. In the case of cysteine-free peptides, the cyclisation step was carried out on the partially-protected linear peptide following cleavage from the 2-chlorotritylchloride resin. After selective cyclisation of the cysteine-free peptides, side-chain deprotection in trifluoroacetic acid followed by preparative RP-MPLC, replacement of the trifluoroacetate ion by acetate and lyophilisation of the acetate form of the peptide was carried out as for cysteine-containing peptides. The molecular masses of the peptides were confirmed by electrospray ionisation mass spectrometry or MALDI-TOF-MS and their purity was determined by analytical high performance liquid chromatography.

The purity of the peptide SEQ ID NO:1 was 96.3%. m/z (ESI) 1924.2 (M++1).

The purity of the peptide SEQ ID NO:2 was 96.3%. m/z. (ESI) 1924.2 (M++1).

The purity of the peptide SEQ ID NO:3 was 98.8%. m/z (ESI) 1888.2 (M++1).

The purity of the peptide SEQ ID NO:4 was 97.4%. m/z (ESI) 1873.4 (M++1).

The purity of the peptide SEQ ID NO:5 was 100%. m/z (MALDI-TOF) 1901.6 (M++1).

The purity of the peptide SEQ ID NO:6 was 100%. m/z (MALDI-TOF) 1902.7 (M++1).

The purity of the peptide SEQ ID NO:7 was 95%. m/z (MALDI-TOF) 1778.02 (M++1).

Example 2—Assessment of Bio-Activity of a Cyclised Compound of the Present Inventio Experiments were carried out on the human epithelial cell line A549 (ATTAC Nr. CCL-185) in passages 80-90. Cells were grown in Dulbecco's modified Eagle's medium/nutrient mixture F12 Ham, supplemented with 10% fetal bovine serum and containing 1% penicillin-streptomycin. All culture media were purchased from Sigma-Aldrich GmbH (St. Louis, MO).

Bio-activity of peptides SEQ ID NO:1 to SEQ ID NO:7 on sodium ion current were studied on A549 cells at room temperature (19-22° C.) 24 to 48 h after plating. Currents were recorded with the patch clamp method in the whole-cell mode. Glass cover slips with the cultured cells were transferred to a chamber of 1 ml capacity, mounted on the stage of an inverted microscope (Zeiss, Axiovert 100). The chamber contained 1 ml of the bath solution of the following composition (in mM): 145 NaCl, 2.7 KCl, 1.8 $CaCl_2$, 2 $MgCl_2$, 5.5 glucose and 10 HEPES, adjusted to pH 7.4 with 1 M NaOH solution. Micropipettes were pulled from thin-walled borosilicate glass capillaries (World Precision Instruments, Inc., FL, USA) with a Flaming Brown micropipette puller (P87, Sutter Instruments, CA, USA) and polished on a microforge (Narishige, Tokyo, Japan) to obtain electrode resistances ranging from 2.0 to 3.5 MΩ. The pipette solution contained (in mM): 135 potassium methane sulphonate, 10 KCl, 6 NaCl, 1 Mg2ATP, 2 NasATP, 10 HEPES and 0.5 EGTA (ethylene glycol tetraacetic acid), adjusted to pH 7.2 with 1 M KOH solution. Chemicals for pipette and bathing solutions were supplied by Sigma-Aldrich (Vienna, Austria). Electrophysiological measurements were carried out with an Axopatch 200B patch clamp amplifier (Axon Instruments, CA, USA). Capacity transients were cancelled, and series resistance was compensated. Whole cell currents were filtered at 5 kHz and sampled at 10 KHz. Data acquisition and storage were processed directly to a PC equipped with pCLAMP 10.0 software (Axon Instruments, CA, USA).

After GΩ-seal formation, the equilibration period of 5 min was followed by control recordings at holding potentials (Eh) between −100 and +100 mV in 20 mV increments for 1 min at each Eh. Then, aliquots of a stock solution, which was prepared with distilled water, were cumulatively added into the bathing solution, resulting in concentrations ranging from 3.5 to 240 nM peptides SEQ ID 1 to 6. The wash-in phase lasted about 1 min. After steady-state had been reached, the same experimental protocol was applied for each concentration of the peptide and during control recordings. Concentration-response curves and EC50-values were fitted and estimated for currents recorded at Eh of −100 mV with SigmaPlot 9.0. Differences in EC50 were calculated for statistical significance ($P<0.05$) with the Student's t-test. For evaluation of ion selectivity, sodium ion current was blocked by 10 to 100 µM amiloride hydrochloride hydrate before the addition of peptides SEQ ID NO:1 to SEQ ID NO:7. Subsequent addition of 10 mM tetraethylammonium chloride (TEA) indicated whether any observed increases in the current were due to potassium current. These experiments were also carried out at Eh=−100 mV.

The results of determining the effect of peptides SEQ ID NO:1 to SEQ ID NO:7 on sodium ion current measured in the patch clamp assay using whole cell recordings are shown in Table III setting out the activity of peptides SEQ ID NO: 1 to SEQ ID NO:7 on cellular sodium ion current in patch clamp assay with A549 cell line using whole cell recording mode. The activity of each peptide in the assay is expressed as $EC_{50}$ (in nM) for each peptide, where $EC_{50}$ is the effective concentration at which 50% of the maximal activity (i.e. maximal increase in current, I) is observed.

TABLE III

| Peptide | $EC_{50}$ (nM) |
| --- | --- |
| SEQ ID 1 | 54 |
| SEQ ID 2 | 56 |
| SEQ ID 3 | 38 |
| SEQ ID 4 | 45 |
| SEQ ID 5 | 24 |
| SEQ ID 6 | 19 |
| SEQ ID 7 | no activity |

The dose-response curves obtained from the patch clamp assay with the cell line A549 using whole cell mode for the peptides SEQ ID NO:1 to SEQ ID NO:6 are shown in FIG. 1, wherein a concentration-response curves of peptides of SEQ ID NO:1 to SEQ ID NO:6 on sodium ion current can be seen. Maximum sodium ion current was set to 100%. For all peptides of SEQ ID 1 to SEQ ID 6 a maximal effect could be observed at 120 nM peptide concentration.

Peptide SEQ ID NO: 7 showed no activity.

Example 3—Effect of Peptides SEQ ID NO:1 to SEQ ID NO:7 on Deglycosylated Cell Surface In whole cell mode experiments as described above, A549 cells were incubated with "PNGase enzyme F" (Peptide-$N^4$-(N-acetyl-$\beta$-D-glucosaminyl)asparagine amidase F) 100 units for 1-5 minutes immediately prior to the patch clamp measurements and glass cover slips with the cultured cells were rinsed with external solution before being transferred to the chamber of the 1 mL bath. After control recordings, 240 nM peptides SEQ ID NO: 1 to SEQ ID NO:7 were added to the bath solution.

Whole cell current was recorded at Eh=−100 mV from cells without any pre-treatment under control conditions and following addition of peptides SEQ ID NO: 1 to SEQ ID NO:7 as well as with pre-treatment with PNGase F.

The results of the deglycosylation experiments using the patch clamp assay in whole cell mode are presented in Table IV, wherein the effect of deglycosylation of A549 cells on activation of sodium ion current by peptides of SEQ ID NO:1 to SEQ ID NO:7 is indicated. Whole cell currents were recorded at Eh=−100 mV. Concentration of peptides of SEQ ID NO: 1 to SEQ ID NO:7 in bath solution was 240 nM.

TABLE IV

| Control/peptide | Pre-treatment with PNGase F | No pre-treatment with PNGase F |
| --- | --- | --- |
| Control | 25.4 pA (n = 16) | |
| SEQ ID NO: 1 | 19.6 pA (n = 3) | 1073.3 ± 15.1 pA (n = 10) |
| SEQ ID NO: 2 | 21.3 pA (n = 3) | |
| SEQ ID NO: 3 | 20.6 pA (n = 3) | |
| SEQ ID NO: 4 | 22.5 pA (n = 3) | |
| SEQ ID NO: 5 | 22.4 pA (n = 3) | |
| SEQ ID NO: 6 | 19.9 pA (n = 3) | |
| SEQ ID NO: 7 | no avtivity | no activity |

The results in Table IV clearly show that pre-treatment of A549 cells with PNGase F prior to the patch clamp assay, abolished the ability of peptides of SEQ ID NO:1 to SEQ ID NO:6 to enhance the sodium current. In control conditions without addition of peptide to the bath solution and at a holding potential of −100 mV, the sodium ion current was 25.4 pA in both untreated cells and cells pre-treated with PNGase F. In untreated cells, addition of peptides SEQ ID NO: 1 to SEQ ID NO:6 (final concentration 240 nM) to the bath solution at a holding potential of −100 mV resulted in a sensitive sodium ion currents of more than 1,000 pA. A peptide of SEQ ID NO:7 showed no activity.

Example 4—Lung Transplantation Experiments with Pigs

Brain death pigs were turned into dorsal position, and a longitudinal sternotomy was performed. The pericardium and both pleural cavities were opened. The superior and inferior caval veins were encircled. An inflow catheter was placed in the pulmonary artery through a purse-string on the right ventricular outflow tract.

Inflow occlusion was obtained by ligating the superior and inferior caval vein, outflow occlusion by clamping the aorta. The lungs (non-ischemic) were then preserved with an ante grade flush of cold isotonic preservation solution (50 ml per kg body weigh of pig, containing potassium ions, sodium ions, magnesium ions, calcium ions, chloride ions, dextran, glucose, buffering ions) through the inflow catheter. Incision of the left auricular appendix provides outflow. The lungs were ventilated during this period with 50% oxygen, and iced slush were placed in both pleural cavities and mediastinum.

The explanation technique was en bloc harvesting with heart and esophagus according to the following steps:
 a) Dissection of soft tissue bridges to the thoracic cavity on both sides of the trachea.
 b) Transsection of both pulmonal ligaments (very deep, difficult exposure), then of the VCI, the lower thoracic descendent aorta and the esophagus, respectively.
 c) Blunt separation from remaining mediastinal adhesions.
 d) Complete inflation of the donor lung prior of tracheal closure with a stapler.

After explantation, the lungs were wrapped in gauze, placed in an insulated ice bag filled with low-potassium dextran extracellular solution, and stored at 4° C. for 18 to 24 hours. A temperature probe was submerged in the container, which will be placed in a refrigerator.

For ex-vivo lung conditioning, the EVLP technique (extravascular lung perfusion) was used. In the EVLP technique, donor lungs are placed into a circuit composed of a pump, ventilator and filters. EVLP technique, the temperature may increased up to 37°C. In the EVLP, a ventilator is used to deliver oxygen to the lungs. The pump is used to perfuse the lungs with an extracellular solution containing human albumin and nutrition. During EVLP, the lung function can be evaluated regularly on key indicators.

For the experimental pig lung transplantation experiments, the EVLP circuit was primed with 2.0 liters of a human albumin solution. This extracellular solution had an optimal colloid osmotic pressure. After the circuit is de-aired, the prime was circulated at 20° C. until it was connected to the lungs. Heparin, cefuroxime methylprednisolone were added to the perfusate.

The preparation of the non-ischemic pig donor lung started with suturing a funnel shaped silastic tube with a pressure monitoring catheter built-in to the left atrial (LA) cuff in order to splint the LA open and to maintain a closed perfusion circuit. This tube was securely anastomosed to the LA cuff using a running 5-0 monofilament suture to provide reliable and effective outflow drainage. The same type cannula was used for cannulation of the pulmonary artery (PA), trimmed as required to match the PA size. A back table retrograde flush was performed using 500 ml of buffered extracellular solution. Before mounting the donor lungs into the EVLP circuit, the trachea was opened and direct bronchial suctioning was performed to clean the airway. An endo-tracheal tube (size 8 mm I.D.) was inserted into the trachea and secured firmly with an umbilical tape. Thereafter the lungs were transferred to the EVLP circuit unit. First, connected the LA cannula to the circuit and initiate slow retrograde flow in order to de-air the PA cannula. Once de-airing was complete, the PA cannula was connected to the circuit and anterograde flow was initiated at 150 ml/min with the perfusate at room temperature. The temperature of the perfusate was then gradually increased to 37° C. over the next 30 minutes. When temperature of 32-34° C. were reached, mechanical ventilation of donor pig lungs was started with the ventilator and the perfusate flow rate was gradually increased.

The flow of EVLP gas supplies oxygen to the lung and it provides carbon dioxide to the inflow perfusate (86% N2, 6% O2, 8% CO2) via the gas exchange membrane was initiated (start at 0.5 L/min gas flow and titrate based on inflow perfusate pCO2) to maintain inflow perfusate pCO2 between 35-45 mmHg. At the time the lungs were fully expanded a single dose of AP301 (1 mg/kg in 5 ml Aqua), using a standard single liquid nebulisation system was applied in the donor pig lung ventilated and perfused by the EVLP circuit system.

During the EVLP experiments, perfusion was constantly evaluated. The following functional parameters were measured and recorded hourly: pulmonary
- artery flow (PAF): L/min
- (mean) pulmonary artery pressure (PAP): mm Hg
- left atrial pressure (LAP): mm Hg
- pulmonary vascular resistance (PVR=[PAP−LAP]×80/PAF): dynes/sec/cm-5
- mean, peak and plateau airway pressure (mAwP, peak AwP, platAwP): cm H2O
- dynamic compliance (mL/cm $H_2O$)
- perfusate gas analysis-inflow (PA) and outflow (PV) PO2, PCO2 and pH.

Results

This study assessed the effect of peptide SEQ ID NO: 1 on lung function in an extra-corporal system simulating non-ischemic donor lung transplantation.

Study results demonstrated that upon inhalative application both dynamic lung compliance and arterio-venous pO2 difference ΔpO2 improved in non-ischemic lungs treated with a peptide of SEQ ID NO: 1 as shown in FIG. 2A and FIG. 2B.

Pulmonary application of a peptide of SEQ ID NO:7 did not provide improving effects on lung function.

Example 5—Lung Transplantation Experiments with Pigs

After the pre-treatment of the non-ischemic donor lungs with peptide SEQ ID NO:1 from Example 4 the lungs were re-implanted in recipient pigs. Shortly after reperfusion of the transplanted lungs peptide SEQ ID NO: 1 was administered.

A left thoracotomy through the sixth inter costal space was done, the left hilus was prepared. The hemiazygos vein on the left side was dissected and transected, as it is hiding both the left pulmonary artery and the left atrium. After dissection the ligated ends can be pulled to facilitate exposure of the OP field. The right pulmonary artery and bronchus are encircled. Left pneumonectomy was performed using vascular clamps. Immediately before the implantation single intravenous dose of methylprednisolone (500-1000 mg) and a low dose of heparin (100 IU/kg, see above) was applied. The donor lung was then reimplanted using 4-0 PDS for the bronchial anastomosis and 5-0 Prolene for the pulmonary artery and the left atrial anastomosis. In pigs, there is an additional lobe (caval lobe) of the right lung with 2 veins into the left atrium (1 separate vein for the caval lobe, 1 additional vein arising from the trunk of the main right lower lobe vein). In the donor left atrium these veins have been closed by sutures during back-table separation to achieve the possibility for a muscular atrial cuff/suture line. Separate clamping of the left part of the left atrium is critical, since it is difficult to find the right plane for the Satinsky clamp. Clamping of the left atrium is poorly tolerated by the pig, therefore the clamp should be released immediately after completion of the atrial anastomosis to reduce post-capillary pulmonary pressure of the right native lung. This was followed by the bronchial anastomosis. The arterial anastomosis was performed with a patch of donor's main pulmonary artery on the recipient pulmonary trunk to ensure a wide anastomosis and a large outflow area for the right ventricle.

After finishing the vascular anastomosis, the implanted lung was flushed retro-, and then ante-grade in a standard manner. Thereafter the arterial clamp was partially released for 10 minutes providing controlled reperfusion.

Care was taken to continue topical hypothermia until reperfusion. Ventilation to the transplanted lung was started during reperfusion by standard mode. Administration of peptide SEQ ID NO:1 by nebulisation (1 mg/kg in 5 ml Aqua) was started at the beginning of ventilation in the recipient animal of the relevant group.

The chest remained open after re-implantation and the transplanted lung was covered with a plastic bag.

The left donor lung was evaluated for an additional period of 24 hours.

The following parameters have been assessed:

Functional assessment of graft function by oxygenation parameters: Arterial blood gas analyses as well as selective blood gas analysis from the left pulmonary veins were performed every 2 hours for 24 h. The respiratory index was calculated: $RI=PaO_2/FiO_2$.

Lung compliance was calculated from the pressure and volume data of the anesthesia ventilator.

Assessment of graft function by estimation of extra vascular lung water by measuring the wet/dry weight ratio.

Functional assessment of graft function by hemodynamic measurements (on-line measurements) and pulmonary vascular resistance (PVR): Hemodynamics, including pulmonary artery pressure (PAP) was measured continuously. Cardiac output (CO) was measured by using a Swan-Ganz catheter. Pulmonary vascular resistance is calculated by the following formula: PVR (dynes·sec−1·cm−5)=(PAP−LAP)×80/CO.

Results

This study assessed the effect of peptide SEQ ID NO:1 on lung function after re-implantation.

The pre-treatment of the non-ischemic donor donor lungs with peptide SEQ ID NO:1 resulted in improved initial graft function and gas exchange, reduced development of lung oedema and reduced rate of ischemia reperfusion injury induced malfunction of the transplanted lung.

SEQUENCE LISTING

```
<160> NUMBER OF SEQ ID NOS: 9

<210> SEQ ID NO 1
<211> LENGTH: 17
<212> TYPE: PRT
<213> ORGANISM: Artificial Sequence
<220> FEATURE:
<223> OTHER INFORMATION: cyclized compound having a disulphide bridge
```

```
<220> FEATURE:
<221> NAME/KEY: DISULFID
<222> LOCATION: (1)..(17)

<400> SEQUENCE: 1

Cys Gly Gln Arg Glu Thr Pro Glu Gly Ala Glu Ala Lys Pro Trp Tyr
1               5                   10                  15
Cys

<210> SEQ ID NO 2
<211> LENGTH: 19
<212> TYPE: PRT
<213> ORGANISM: Artificial Sequence
<220> FEATURE:
<223> OTHER INFORMATION: cyclized compound having an amide bond formed
      between the amino group attached to the epsilon-C atom of the
      lysine residue and the side chain carboxyl group attached to the
      gamma-C of the glutamic acid residue

<400> SEQUENCE: 2

Lys Ser Pro Gly Gln Arg Glu Thr Pro Glu Gly Ala Glu Ala Lys Pro
1               5                   10                  15
Trp Tyr Glu

<210> SEQ ID NO 3
<211> LENGTH: 17
<212> TYPE: PRT
<213> ORGANISM: Artificial Sequence
<220> FEATURE:
<223> OTHER INFORMATION: cyclized compound having an amide bond formed
      between the amino group attached to the epsilon-C atom of the side
      chain of the lysine residue and the carboxyl group of the glycine
      residue

<400> SEQUENCE: 3

Lys Gly Gln Arg Glu Thr Pro Glu Gly Ala Glu Ala Lys Pro Trp Tyr
1               5                   10                  15
Gly

<210> SEQ ID NO 4
<211> LENGTH: 17
<212> TYPE: PRT
<213> ORGANISM: Artificial Sequence
<220> FEATURE:
<223> OTHER INFORMATION: cyclized compound having an amide bond formed
      between the amino group attached to the delta-C of the side chain
      of the ornithine residue and the carboxyl group of the glycine
      residue
<220> FEATURE:
<221> NAME/KEY: MOD_RES
<222> LOCATION: (1)..(1)
<223> OTHER INFORMATION: X = ornithine

<400> SEQUENCE: 4

Xaa Gly Gln Arg Glu Thr Pro Glu Gly Ala Glu Ala Lys Pro Trp Tyr
1               5                   10                  15
Gly

<210> SEQ ID NO 5
<211> LENGTH: 17
<212> TYPE: PRT
<213> ORGANISM: Artificial Sequence
<220> FEATURE:
<223> OTHER INFORMATION: cyclized compound having an amide bond formed
      between the amino group of the 4-aminobutanoic acid residue and
      the side chain carboxyl group attached to the beta-C of the
      aspartic acid residue
```

```
<220> FEATURE:
<221> NAME/KEY: MOD_RES
<222> LOCATION: (1)..(1)
<223> OTHER INFORMATION: X = 4-aminobutanoic acid

<400> SEQUENCE: 5

Xaa Gly Gln Arg Glu Thr Pro Glu Gly Ala Glu Ala Lys Pro Trp Tyr
1               5                   10                  15
Asp

<210> SEQ ID NO 6
<211> LENGTH: 17
<212> TYPE: PRT
<213> ORGANISM: Artificial Sequence
<220> FEATURE:
<223> OTHER INFORMATION: cyclized compound having an amide bond formed
      between the amino group of the beta-alanine residue and the side
      chain carboxyl group attached to the gamma-C of the glutamic acid
      residue
<220> FEATURE:
<221> NAME/KEY: MOD_RES
<222> LOCATION: (1)..(1)
<223> OTHER INFORMATION: X = beta-alanine

<400> SEQUENCE: 6

Xaa Gly Gln Arg Glu Thr Pro Glu Gly Ala Glu Ala Lys Pro Trp Tyr
1               5                   10                  15
Glu

<210> SEQ ID NO 7
<211> LENGTH: 17
<212> TYPE: PRT
<213> ORGANISM: Artificial Sequence
<220> FEATURE:
<223> OTHER INFORMATION: cyclized compound having a disulphide bridge
<220> FEATURE:
<221> NAME/KEY: DISULFID
<222> LOCATION: (1)..(17)

<400> SEQUENCE: 7

Cys Gly Gln Arg Glu Ala Pro Ala Gly Ala Ala Ala Lys Pro Trp Tyr
1               5                   10                  15
Cys

<210> SEQ ID NO 8
<211> LENGTH: 17
<212> TYPE: PRT
<213> ORGANISM: Artificial Sequence
<220> FEATURE:
<223> OTHER INFORMATION: cyclized compound of formula I
<220> FEATURE:
<221> NAME/KEY: MOD_RES
<222> LOCATION: (1)..(1)
<223> OTHER INFORMATION: X = selected from Cys; Lys-Ser-Pro; Lys;
      ornithine, 4-amino butanoic acid; beta-alanine
<220> FEATURE:
<221> NAME/KEY: MOD_RES
<222> LOCATION: (17)..(17)
<223> OTHER INFORMATION: X = selected from Cys; Asp; Gly; Glu

<400> SEQUENCE: 8

Xaa Gly Gln Arg Glu Thr Pro Glu Gly Ala Glu Ala Lys Pro Trp Tyr
1               5                   10                  15
Xaa

<210> SEQ ID NO 9
<211> LENGTH: 17
```

```
<212> TYPE: PRT
<213> ORGANISM: Artificial Sequence
<220> FEATURE:
<223> OTHER INFORMATION: cyclized compound of formula I
<220> FEATURE:
<221> NAME/KEY: MOD_RES
<222> LOCATION: (1)..(1)
<223> OTHER INFORMATION: X = an amino acid or amino acid sequence with 1
      to 4 members selected from natural or unnatural amino acids
<220> FEATURE:
<221> NAME/KEY: MOD_RES
<222> LOCATION: (1)..(1)
<223> OTHER INFORMATION: X = an amino acid or amino acid sequence with 1
      to 4 members selected from natural or unnatural amino acids
<220> FEATURE:
<221> NAME/KEY: MOD_RES
<222> LOCATION: (17)..(17)
<223> OTHER INFORMATION: X = a natural amino acid

<400> SEQUENCE: 9

Xaa Gly Gln Arg Glu Thr Pro Glu Gly Ala Glu Ala Lys Pro Trp Tyr
1               5                   10                  15

Xaa
```

The invention claimed is:

1. A method of improving the dynamic lung compliance and arterio-venous $pO_2$ difference of a donor lung extracorporeally during ventilating and perfusing of the donor lung, the method comprising:

conditioning the donor lung extracorporeally prior to implantation to improve ventilation performance of the donor lung, wherein conditioning of the donor lung comprises applying into said donor lung ex vivo a cyclized compound of the amino acid sequence (SEQ ID NO: 9) of formula I:

$$X_1\text{-GQRETPEGAEAKPWY-}X_2 \quad (I)$$

wherein, $X_1$ comprises an amino acid sequence with 1 to 4 members, comprising natural or unnatural amino acids, and $X_2$ comprises one amino acid, selected from natural amino acids, and wherein the compound is applied into the donor lung during ventilating and perfusing of said donor lung.

2. The method according to claim 1 wherein $X_1$ in a compound of formula I is selected from the group consisting of C, KSP, K, ornithine, 4-amino butanoic acid, and β-alanine.

3. The method according to claim 1, wherein $X_2$ is selected from the group consisting of C, D, G, and E.

4. The method according to claim 1, wherein cyclization of the cyclized compound is between the first amino acid residue in $X_1$ and the last amino acid residue in $X_2$.

5. The method according to claim 1, wherein cyclization of the cyclized compound is via an amide bond or via a disulfide bridge.

6. The method according to claim 1, wherein the compound of formula I is selected from the group consisting of:

SEQ ID NO: 1
Cyclo(CGQRETPEGAEAKPWYC)

wherein both terminal cysteine residues form a disulfide bridge;

SEQ ID NO: 2
Cyclo(KSPGQRETPEGAEAKPWYE)

wherein an amide bond is formed between the amino group attached to the ε-carbon atom of the N-terminal lysine residue and the side chain carboxyl group attached to the γ-carbon of the C-terminal glutamic acid residue;

SEQ ID NO: 3
Cyclo(KGQRETPEGAEAKPWYG)

wherein an amide bond is formed between the amino group attached to the ε-carbon atom of the side chain of the N-terminal lysine residue and the carboxyl group of the C-terminal glycine residue;

SEQ ID NO: 4
Cyclo(ornithine-GQRETPEGAEAKPWYG)

wherein an amide bond is formed between the amino group attached to the δ-carbon of the side chain of the N-terminal ornithine residue and the carboxyl group of the C-terminal glycine residue;

SEQ ID NO: 5
Cyclo(4-aminobutanoic acid-GQRETPEGAEAKPWYD)

wherein an amide bond is formed between the amino group of the N-terminal 4-aminobutanoic acid residue and the side chain carboxyl group attached to the β-carbon of the C-terminal aspartic acid residue; and SEQ ID NO: 6
Cyclo(β-alanine-GQRETPEGAEAKPWYE)

wherein an amide bond is formed between the amino group of the N-terminal β-alanine residue and the side chain carboxyl group attached to the γ-carbon of the C-terminal glutamic acid residue.

7. The method according to claim 1, wherein the cyclized compound of formula I is in the form of a salt.

8. The method according to claim 1, wherein the cyclized compound of formula I is administered by spraying.

9. The method according to claim 1, wherein the cyclized compound of formula I is administered by use of a nebulizer.

10. The method according to claim 1 wherein $X_1$ comprises an amino acid sequence with 1 to 3 members, comprising natural or unnatural amino acids.

11. The method of claim 1, wherein the donor lung comprises a $pO_2$ greater than 100 mm Hg.

12. The method of claim 11, further comprising nebulizing the cyclized compound into the donor lung during ventilation, prior to implantation.

13. A method of improving the dynamic lung compliance and arterio-venous $pO_2$ difference of a human donor lung extracorporeally, comprising:
conditioning the human donor lung extracorporeally prior to implantation to improve ventilation performance of the human donor lung, wherein conditioning of the human donor lung comprises treating the human donor lung ex vivo prior to implantation with a nebulized treatment composition comprising a cyclized compound of the amino acid sequence (SEQ ID NO: 9) of formula I:

$$X_1\text{-GQRETPEGAEAKPWY-}X_2 \quad (I)$$

wherein, $X_1$ comprises an amino acid sequence with 1 to 4 members, comprising natural or unnatural amino acids, and $X_2$ comprises one amino acid, selected from natural amino acids, and wherein the compound is applied into the human donor lung together with ventilating and perfusing said human donor lung.

14. A method of improving the dynamic lung compliance and arterio-venous $pO_2$ difference of a donor lung, comprising:

conditioning the donor lung extracorporeally prior to implantation to improve ventilation performance of the donor lung, wherein conditioning of the donor lung comprises treating the donor lung with an aerosol comprising a cyclized compound of the amino acid sequence (SEQ ID NO: 9) of formula I:

$$X_1\text{-GQRETPEGAEAKPWY-}X_2 \quad (I)$$

wherein, $X_1$ comprises an amino acid sequence with 1 to 4 members, comprising natural or unnatural amino acids, and $X_2$ comprises one amino acid, selected from natural amino acids, and wherein the compound is applied into the donor lung together with ventilating and perfusing said donor lung.

15. The method according to claim 14, wherein treating the donor lung occurs immediately before implantation of the donor lung into a recipient.

* * * * *